(12) United States Patent
Diana

(10) Patent No.: US 12,565,634 B2
(45) Date of Patent: Mar. 3, 2026

(54) SPARGER ASSEMBLIES FOR A BIOPROCESSING SYSTEM

(71) Applicant: GLOBAL LIFE SCIENCES SOLUTIONS USA LLC, Marlborough, MA (US)

(72) Inventor: Rafael Diana, Marlborough, MA (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 735 days.

(21) Appl. No.: 17/947,537

(22) Filed: Sep. 19, 2022

(65) Prior Publication Data

US 2024/0093137 A1      Mar. 21, 2024

(51) Int. Cl.
*C12M 1/00* (2006.01)
*C12M 1/06* (2006.01)

(52) U.S. Cl.
CPC ............ *C12M 29/06* (2013.01); *C12M 23/14* (2013.01); *C12M 23/26* (2013.01); *C12M 27/02* (2013.01)

(58) Field of Classification Search
CPC ...................................................... C12M 29/06
See application file for complete search history.

(56) References Cited

U.S. PATENT DOCUMENTS 5,030,362 A    7/1991  Da Silva et al.
7,985,574 B2   7/2011  Brahmbhatt 2011/0101548 A1    5/2011  Kim et al.
2014/0271413 A1    9/2014  Frianeza-Kullberg
2021/0147781 A1*   5/2021  Nakai .................... C12M 29/18

FOREIGN PATENT DOCUMENTS

CN          103224876         7/2013
WO          2017221346       12/2017
WO      WO-2020120251 A2 *  6/2020  ............ C12M 29/06

OTHER PUBLICATIONS

International Search Report dated Feb. 23, 2024 from corresponding PCT/EP2023/075132.
International Search Report dated Jan. 2, 2024 from corresponding PCT/EP2023/075132.

* cited by examiner

*Primary Examiner* — Jonathan M Hurst
(74) *Attorney, Agent, or Firm* — Grogan, Tuccillo & Vanderleeden, LLP

(57) ABSTRACT

A sparger assembly for a bioprocessing system includes a base and a plurality of spargers connected to the base, each sparger including a plurality of pores, the plurality of spargers each have a generally cylindrical shape. Each of the plurality of spargers includes a sidewall and a top, which define the cylindrical shape, the sidewall and the top each include a plurality of pores. The pores of the sidewall can be arranged around a circumference of the sidewall at an array of heights. Ridges may also be located on the sidewall above a respective array of pores.

14 Claims, 10 Drawing Sheets

SPARGER ASSEMBLIES FOR A BIOPROCESSING SYSTEM

BACKGROUND

Technical Field

Embodiments of the invention relate generally to bioprocessing systems and methods and, more particularly, to sparger assemblies for single-use bioreactor systems.

Discussion of Art

A variety of vessels, devices, components and unit operations are known for carrying out biochemical and/or biological processes and/or manipulating liquids and other products of such processes. In order to avoid the time, expense, and difficulties associated with sterilizing the vessels used in biopharmaceutical manufacturing processes, single-use or disposable bioreactor bags and single-use mixer bags are used as such vessels. For instance, biological materials (e.g., animal and plant cells) including, for example, mammalian, plant or insect cells and microbial cultures can be processed using disposable or single-use mixers and bioreactors.

Increasingly, in the biopharmaceutical industry, single use or disposable containers are used. Such containers can be flexible or collapsible plastic bags that are supported by an outer rigid structure such as a stainless steel shell or vessel. Use of sterilized disposable bags eliminates time-consuming step of cleaning of the vessel and reduces the chance of contamination. The bag may be positioned within the rigid vessel and filled with the desired fluid for mixing. An agitator assembly disposed within the bag is used to mix the fluid. Existing agitators are either top-driven (having a shaft that extends downwardly into the bag, on which one or more impellers are mounted) or bottom-driven (having an impeller disposed in the bottom of the bag that is driven by a magnetic drive system or motor positioned outside the bag and/or vessel). Most magnetic agitator systems include a rotating magnetic drive head outside of the bag and a rotating magnetic agitator (also referred to in this context as the "impeller") within the bag. The movement of the magnetic drive head enables torque transfer and thus rotation of the magnetic agitator allowing the agitator to mix a fluid within the vessel. Magnetic coupling of the agitator inside the bag, to a drive system or motor external to the bag and/or bioreactor vessel, can eliminate contamination issues, allow for a completely enclosed system, and prevent leakage. Because there is no need to have a drive shaft penetrate the bioreactor vessel wall to mechanically spin the agitator, magnetically coupled systems can also eliminate the need for having seals between the drive shaft and the vessel.

Depending on the fluid being processed, the bioreactor system may include a number of fluid lines and different sensors, probes and ports coupled with the bag for monitoring, analytics, sampling, and liquid transfer. For example, a harvest port is typically located at the bottom of the disposable bag and the vessel, and allows for a harvest line to be connected to the bag for harvesting and draining of the bag. In addition, existing bioreactor systems typically utilize spargers for introducing a controlled amount of a specific gas or combination of gases into the bioreactor. A sparger outputs small gas bubbles into a liquid in order to agitate and/or dissolve the gas into the liquid. The delivery of gas via spargers helps in mixing a substance, maintaining a homogenous environment throughout the interior of the bag, and is sometimes essential for growing cells in a bioreactor. Ideally, the spargers and the agitator are in close proximity to ensure optimal distribution of the gases throughout the container.

In connection with the above, in cell culture, oxygen is a key substrate for growth, production, and maintenance activities. Cells obtain their oxygen in free and noncompound forms, called dissolved oxygen (DO). One of the most important functions of bioreactors is continuously providing dissolved oxygen to cells through aeration. Aeration in the bioreactor typically occurs when oxygen diffuses through overlay to the cell culture medium interface and when oxygen from the spargers dissolve in the cell culture through convection with the help of agitation. Agitation disperses the oxygen bubbles and promotes mass transfer of the gas bubbles through the gas liquid (cell culture medium) interface. The rate of oxygen transfer (OTR) from gas to liquid interface is a function of physicochemical properties of the cell culture medium, the geometrical parameters of the bioreactor, and presence of cells.

Due to its low solubility in liquid phase and increasing metabolic consumption by the cells with time, oxygen is supplied continuously to the cell culture. Oxygen supply is carefully controlled for optimal cell growth by manipulating bioreactor parameters. During batch cell culture, oxygen utilization rate (OUR)(or rate of oxygen transfer (OTR)) is initially low during the lag phase, where cells are self synthesizing and there is little gain of cell density. As cell density increases during the exponential phase, OUR increases until OTR becomes a limiting rate, as determined by the mass transfer of oxygen into the bulk liquid. The OTR and OUR rates are correlated by the oxygen mass transfer coefficient, kLa (the volumetric mass-transfer coefficient that describes the efficiency with which oxygen can be delivered to a bioreactor for a given set of operating conditions). Therefore, the OTR, through its correlation to kLa, defines a theoretical maximum cell density that could be achieved in cell culture.

Higher oxygen availability drives kLa increases. Increasing oxygen supply to a bioreactor drives this availability and can be controlled by modifying concentration (air vs $O_2$ enrichment) and volumetric flow. Although high kLa values are desirable, it is important to consider the actual operating conditions and implications to cell viability and associated process costs.

For example, high air flow rates can cause cell damage due to shear forces. Excessive foam might also be generated, requiring a high concentration of antifoam that could hinder downstream processing. Additionally, higher air flow rates require a larger exhaust filter area, driving consumable cost increases.

It is therefore clear that high performance bioreactor systems must provide good bulk mixing in combination with efficient gas dispersion in order to achieve a high gas surface area and bubble size distribution, and thus provide high oxygen transfer rates and kLa values desired in intensified cell culture and/or microbial applications. However, there is a need for an improved sparger that provides high kLa while maintaining acceptable aeration flow rates.

BRIEF DESCRIPTION

According to a first aspect of the invention, a sparger assembly for a bioprocessing system is provided. The sparger assembly includes a base; and a plurality of spargers connected to the base, each sparger including a plurality of pores; wherein the plurality of spargers each have a generally cylindrical shape.

In embodiments, each of the plurality of spargers includes a sidewall and a top, which define the cylindrical shape. The sidewall and the top each include a plurality of pores.

In embodiments, the pores of the sidewall include a first array of pores located at a first height from a top surface of the base. In further embodiments, the pores of the sidewall further include a second array of pores located at a second height from a top surface of the base, the second height be different than the first height. The second array of pore are radially offset in relation to the first array of pores.

In embodiments, the sidewall includes a first ridge extending at least partially around a circumference of the sidewall, the first ridge located above the first array of pores. In further embodiments, the sidewall further includes a second ridge extending at least partially around a circumference of the sidewall, the second ridge located above the second array of pores.

In embodiments, each of the plurality of spargers includes two bonding surfaces, the two bonding surfaces configured to bond with the base upon application of heat and/or vibratory forces.

According to a second aspect of the invention, an impeller and sparger assembly for a bioprocessing system is provided. The bioprocessing system includes and impeller and sparger assembly. The sparger assembly includes a base; and a plurality of spargers connected to the base, each sparger including a plurality of pores; wherein the plurality of spargers each have a generally cylindrical shape. Each of the plurality of spargers includes a sidewall and a top, which define the cylindrical shape. The sidewall and the top each include a plurality of pores. In embodiments, the pores of the sidewall include a first array of pores located at a first height from a top surface of the base. In further embodiments, the pores of the sidewall further include a second array of pores located at a second height from a top surface of the base, the second height be different than the first height. The second array of pore are radially offset in relation to the first array of pores. In embodiments, the sidewall includes a first ridge extending at least partially around a circumference of the sidewall, the first ridge located above the first array of pores. In further embodiments, the sidewall further includes a second ridge extending at least partially around a circumference of the sidewall, the second ridge located above the second array of pores. In embodiments, each of the plurality of spargers includes two bonding surfaces, the two bonding surfaces configured to bond with the base upon application of heat and/or vibratory forces. The impeller assembly includes a magnetic hub connected to the base; and an impeller connected to the magnetic hub.

According to a third aspect of the invention, a bioprocessing apparatus is provided. The bioprocessing apparatus includes a flexible bag, a sparging assembly, and an impeller assembly. The sparger assembly includes a base; and a plurality of spargers connected to the base, each sparger including a plurality of pores; wherein the plurality of spargers each have a generally cylindrical shape. Each of the plurality of spargers includes a sidewall and a top, which define the cylindrical shape. The sidewall and the top each include a plurality of pores. In embodiments, the pores of the sidewall include a first array of pores located at a first height from a top surface of the base. In further embodiments, the pores of the sidewall further include a second array of pores located at a second height from a top surface of the base, the second height be different than the first height. The second array of pore are radially offset in relation to the first array of pores. In embodiments, the sidewall includes a first ridge extending at least partially around a circumference of the sidewall, the first ridge located above the first array of pores. In further embodiments, the sidewall further includes a second ridge extending at least partially around a circumference of the sidewall, the second ridge located above the second array of pores. In embodiments, each of the plurality of spargers includes two bonding surfaces, the two bonding surfaces configured to bond with the base upon application of heat and/or vibratory forces. The impeller assembly includes a magnetic hub connected to the base; and an impeller connected to the magnetic hub. The base includes at least one input port, the at least one input port in fluid communication with the plurality of spargers. The input port is connectable to a gas source such that gas from the gas source is configured to exit through the plurality of pores and into the flexible bag.

DRAWINGS

The present invention will be better understood from reading the following description of non-limiting embodiments, with reference to the attached drawings, wherein below:

DETAILED DESCRIPTION

Figure 1:
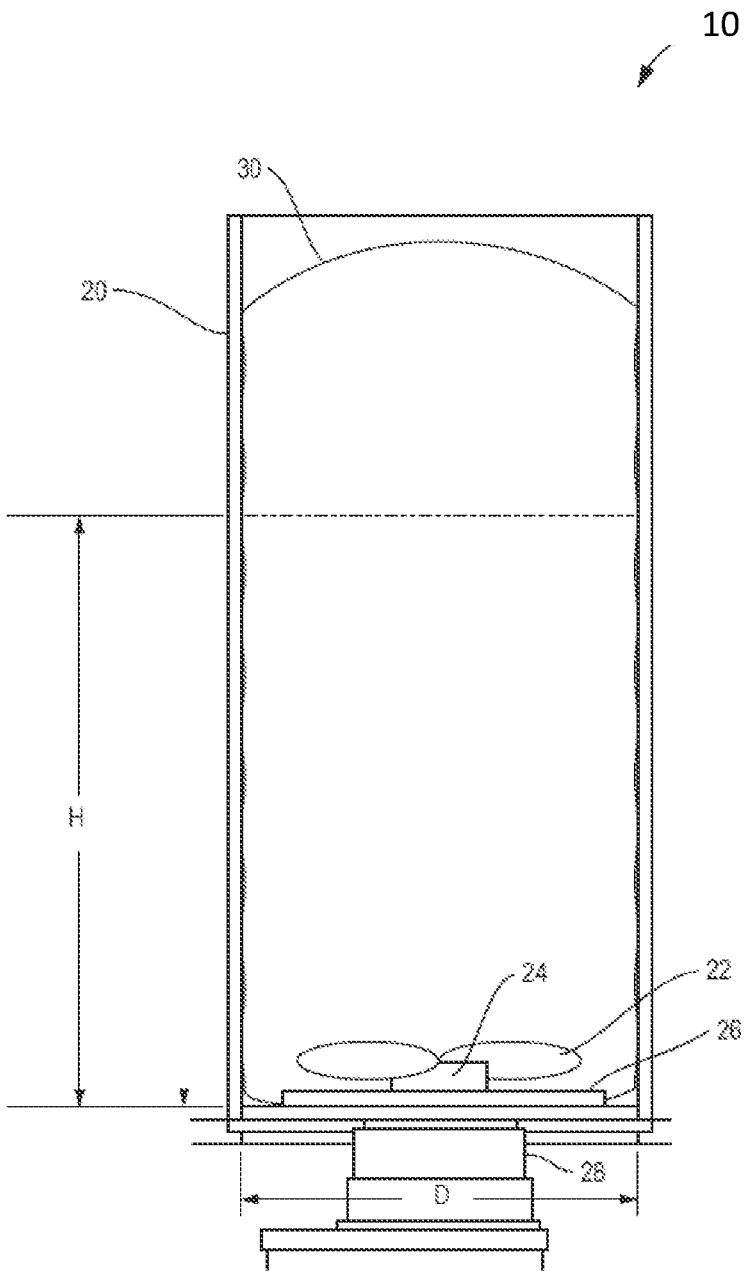
FIG. 1 is a cross-sectional view of a bioreactor system according to an embodiment of the invention.

Reference will be made below in detail to exemplary embodiments of the invention, examples of which are illustrated in the accompanying drawings. Wherever possible, the same reference characters used throughout the drawings refer to the same or like parts.

As used herein, the term "flexible" or "collapsible" refers to a structure or material that is pliable, or capable of being bent without breaking, and may also refer to a material that is compressible or expandable. An example of a flexible structure is a bag formed of polyethylene film. The terms "rigid" and "semi-rigid" are used herein interchangeably to describe structures that are "non-collapsible," that is to say structures that do not fold, collapse, or otherwise deform under normal forces to substantially reduce their elongate dimension. Depending on the context, "semi-rigid" can also denote a structure that is more flexible than a "rigid" element, e.g., a bendable tube or conduit, but still one that does not collapse longitudinally under normal conditions and forces.

A "vessel," as the term is used herein, means a flexible bag, a flexible container, a semi-rigid container, a rigid container, or a flexible or semi-rigid tubing, as the case may be. The term "vessel" as used herein is intended to encompass bioreactor vessels having a wall or a portion of a wall that is flexible or semi-rigid, single use flexible bags, as well as other containers or conduits commonly used in biological or biochemical processing, including, for example, cell culture/purification systems, mixing systems, media/buffer preparation systems, and filtration/purification systems, e.g., chromatography and tangential flow filter systems, and their associated flow paths. As used herein, the term "bag" means a flexible or semi-rigid container or vessel used, for example, as a bioreactor or mixer for the contents within.

With reference to FIG. 1, a bioreactor system 10 according to an embodiment of the invention is illustrated. The bioreactor system 10 includes a generally rigid bioreactor vessel or support structure 20. The vessel 20 may be formed, for example, from stainless steel, polymers, composites, glass, or other metals, and may be cylindrical in shape, although other shapes may also be utilized without departing from the broader aspects of the invention. The vessel 20 provides support to a single-use, flexible bag 30 disposed within the vessel 20. The vessel 20 can be any shape or size as long as it is capable of supporting a single-use flexible bioreactor bag 30. For example, according to one embodiment of the invention the vessel 20 is capable of accepting and supporting a 10-2000 L flexible or collapsible bioprocess bag assembly 30, and has a maximum working volume height H and inner diameter D.

The vessel 20 may include one or more sight windows, which allows one to view a fluid level within the flexible bag 30, as well as a window positioned at a lower area of the vessel 20. The window allows access to the interior of the vessel 20 for insertion and positioning of various sensors and probes (not shown) within the flexible bag 30, and for connecting one or more fluid lines to the flexible bag 30 for fluids, gases, and the like, to be added or withdrawn from the flexible bag 20. Sensors/probes and controls for monitoring and controlling important process parameters include any one or more, and combinations of: temperature, pressure, pH, dissolved oxygen (DO), dissolved carbon dioxide (pCO$_2$), mixing rate, and gas flow rate, for example.

The flexible bag 20 contains an impeller 22 attached to a magnetic hub 24 at the bottom center of the inside of the bag, which rotates on an impeller plate 26 (herein also referred to as "base plate" or "sparger plate") also positioned on the inside bottom of the bag 20. Together, the impeller 22 and hub 24 (and in some embodiments, the impeller plate 26) form an impeller assembly. A magnetic drive 28 external to the vessel 20 provides the motive force for rotating the magnetic hub 24 and impeller 22 to mix the contents of the flexible bag 30. While FIG. 1 illustrates the use of a magnetically-driven impeller, other types of impellers and drive systems are also possible, including top-driven impellers.

In an embodiment, the impeller plate 26 may be configured as a sparger assembly that is used to introduce a specific gas or air into the fluid within the bag 30 in order to agitate and/or dissolve the air or gas into the fluid. Accordingly, in some embodiments, the impeller and sparger, and the components thereof, form a combined impeller/sparger assembly. In other embodiments, the sparger assembly and the impeller assembly may be separate and/or discrete components. In either implementation, the sparger assembly and the impeller assembly are in close proximity to ensure optimal distribution of gases throughout the bag 30, as discussed in detail hereinafter. As discussed below, it is envisioned that the sparger assembly (which may also serve as an impeller plate supporting the impeller) may take one of various configurations.

Figures 2A, 2B:
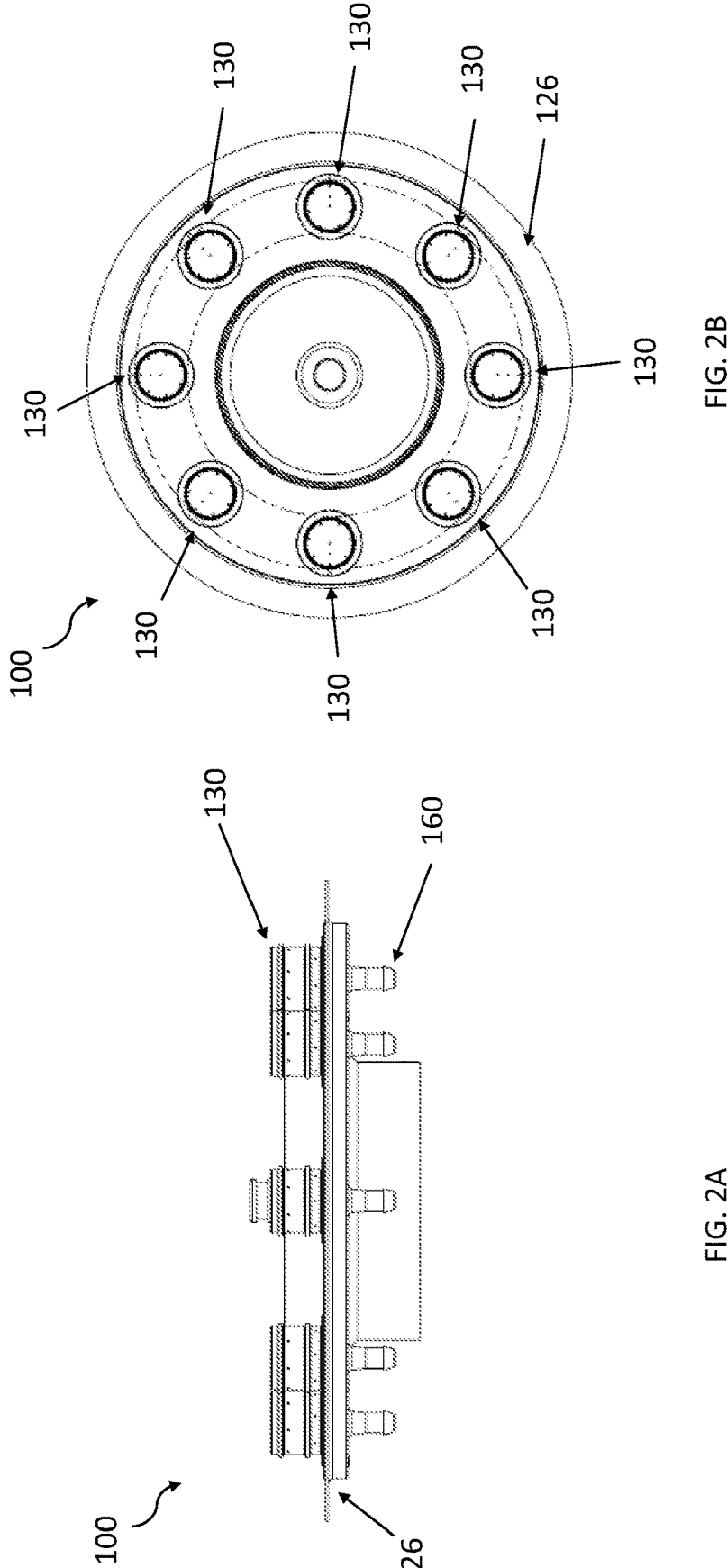
FIGS. 2A and 2B illustrate side and top views of a sparging assembly, according to embodiments of the invention.
Figure 3:
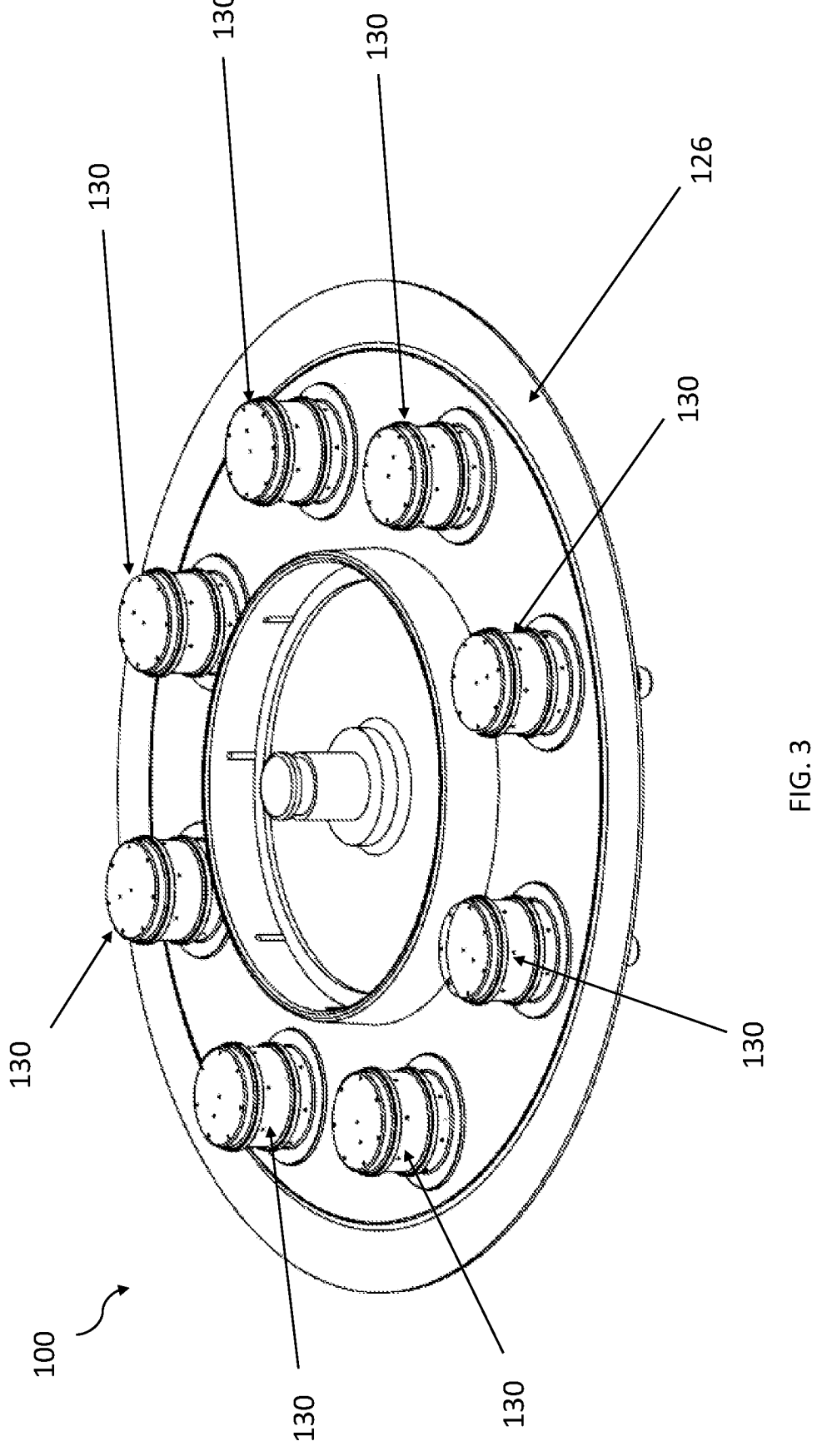
FIG. 3 illustrates a perspective view of the sparging assembly of FIGS. 2A and 2B.
Figure 4:
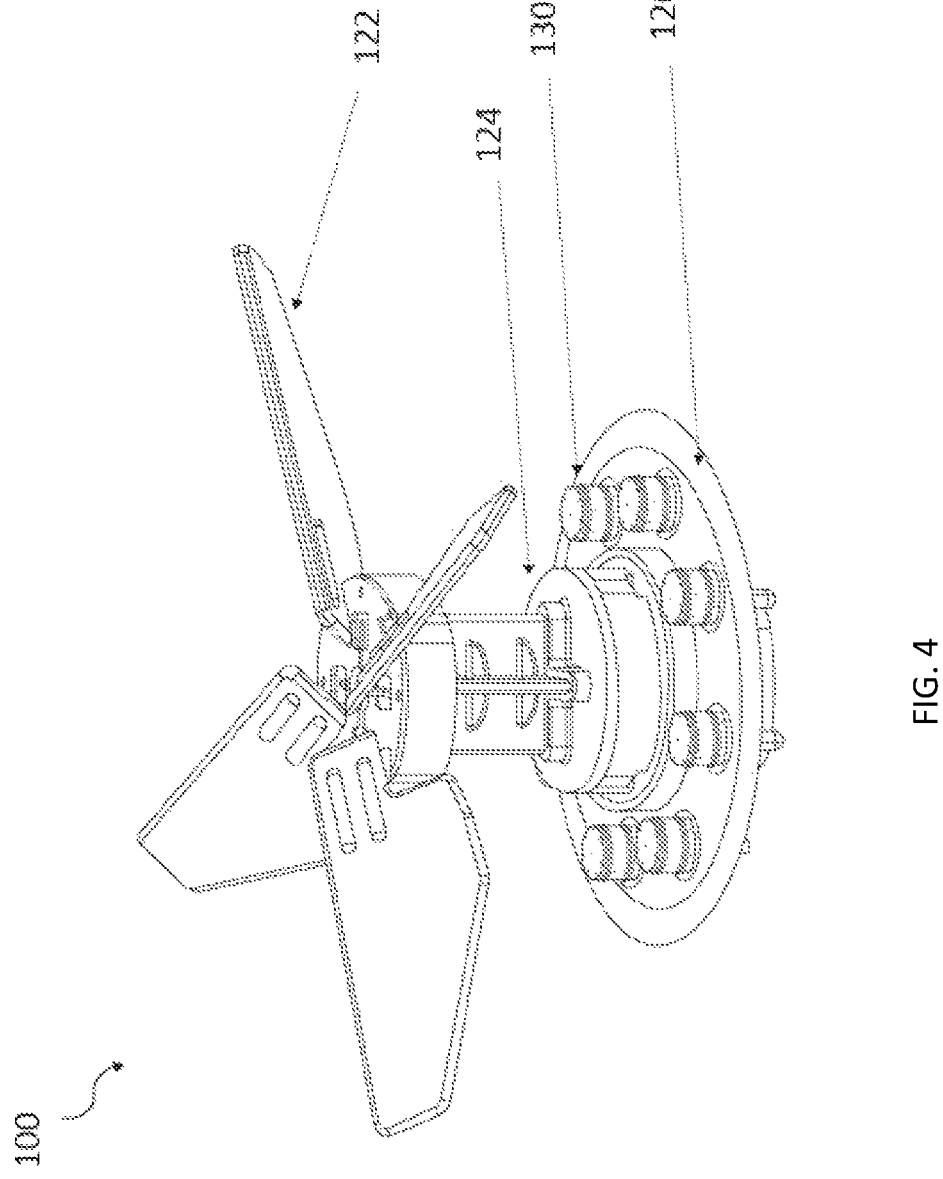
FIG. 4 illustrates an impeller and sparger assembly, incorporating the sparging assembly of FIGS. 2A-3, according to embodiments of the invention.
Figure 5B:
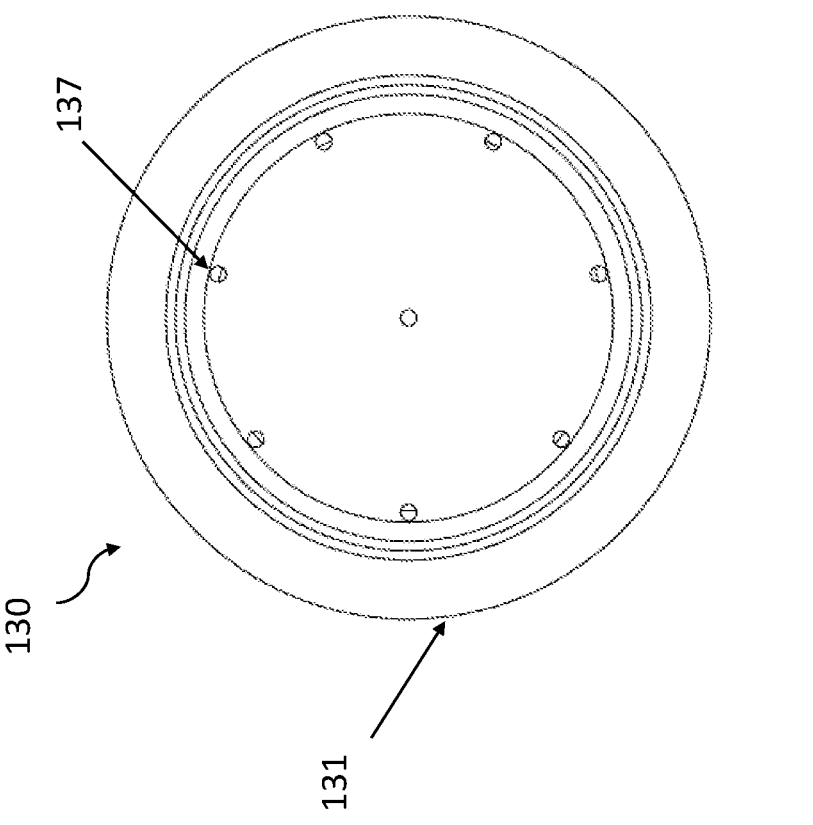
FIGS. 5A and 5B illustrate side and top views of a sparger, of the sparging assembly of FIGS. 2A-3, according to embodiments of the invention.
Figure 5A:
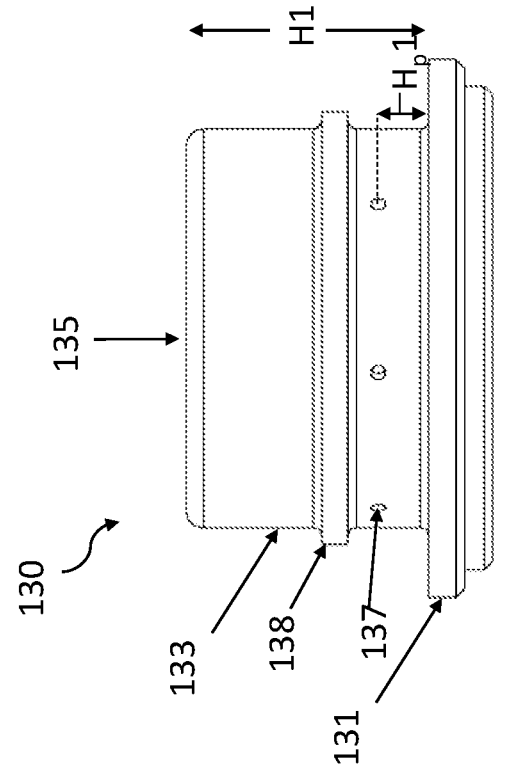

For example, FIGS. 2A-3 illustrate an embodiment of a sparger assembly 100 that may be utilized with the flexible bag 30 and bioreactor system 10. As shown therein, the sparger assembly 100 includes a baseplate 126 and a plurality of spargers 130 connected to the baseplate 126. The spargers 130 are each generally cylindrically shaped, and concentrically located around a perimeter of the baseplate 162. Each sparger 130 is connected to a fluid input port 160, such that a gas/fluid can be introduced through the spargers 130 and into the flexible bag 30. In embodiments, the spargers 130 and baseplate 126 may be manufactured as an integral, unitary component. In other embodiments, the spargers 130 may be manufactured as separate components that may be coupled to the baseplate 126. While FIGS. 2A-3 illustrate eight spargers 130 spaced equidistantly around the baseplate 126, more or fewer spargers 130 (e.g., one to seven or more than eight) are within the scope of the invention. Spargers 130 include an array of pores, such that when a gas is input through input ports 160 the gas exits the spargers 130 and form bubbles of a controlled size. As FIG. 4. illustrates, the bubbles created by the spargers 130 are then dispersed by the impeller 122 as it is rotated due to the magnetic force generated by the magnetic drive 28 spinning the magnetic hub 124.

As will be described in greater detail below, traditional spargers are planar in nature (e.g., in the form of flat discs or rings) and are thus limited in the amount of gas that can be introduced into a cell culture. This limitation results in an inadequate amount of gas being fed into the bioreactor. As a result, the bioreactor cannot provide sufficient oxygen kLa and/or CO2 stripping, resulting in poorer performance (e.g., high cell death and lower cell density). As compared to traditional spargers, the present invention has advantageously found that by making the spargers in a three-dimensional shape (e.g., in a cylindrical shape), additional pores can be implemented, which allows for a larger number of smaller bubbles to form when gas is introduced into the spargers (when the bag is filled with a fluid, such as cell culture media). A higher bubble density, with smaller bubble size, provides more surface area contact between the sparged gas and the fluid, which greater improves oxygen kLa or CO2 stripping. Additionally, the design of the spargers of the present invention is such that bubble coalescence (i.e., bubbles joining together to form larger bubbles) is reduced, helping to ensure that many small bubbles are homogenously dispersed into the cell culture medium during a bioprocessing operation within the bioreactor (e.g., cell culturing).

FIGS. 5A-7 illustrate side, top, cross-sectional and perspective views of a sparger 130, according to embodiments of the invention. Sparger 130 includes a base 131, with a sidewall 133 that projects up a height H1 from a top surface of the base 131. The sidewall 133 terminates at a top 135, which is a generally planar surface. As these figures illustrate, base 131 is generally circular in shape, and the sidewall 133 is cylindrically shaped, having a diameter that is less than the diameter of base 131 (although the diameters of the sidewall 133 and base 131 may be the same, or the diameter of the sidewall 133 can be larger than the diameter of the sidewall 131). The sidewall 131 include pores 137 such that an introduced gas can bubble out of the sparger 130. In particular embodiments, sidewall 133 includes an array of pores 137 in a circular pattern at a height $H_p1$. In alternative embodiments, the array of pores 137 in the sidewall have varying heights from the base. Additionally, the top 135 includes an array of pores 137 in a circular pattern around its perimeter, with an additional central pore. It is noted that the pores 137 located around the perimeter of the top 135 are radially offset from the pores located in the sidewall (see, e.g., FIG. 6A). By radially offsetting the pores there is a lower likelihood that bubbles coalesce. Said another way, as bubbles form and exit the sidewall 133 they travel vertically upward. These bubbles are less likely to encounter bubbles formed by the pores in the top 135 because they are radially offset from one another (i.e., not located in parallel along a longitudinal axis of the sparger 130), thus reducing the likelihood of coalescence. While it is noted that in one specific embodiment, there are seven circumferential pores and one central pore in the top 135, more or fewer pores are within the scope of the invention. Similarly, while the drawings illustrate seven pores in a circular pattern at a height $H_p1$, additional or fewer pores are within the scope of the invention.

Sparger 130 also includes a ridge 138 that extends at least partially around the sidewall 133. Ridge 138 is located above the array of pores 137 located in the sidewall 133 and serves as a mechanism to guide the bubbles formed by the pores 137. Specifically, as the bubbles form and exit the sidewall 133 they make contact with a bottom surface of the ridge 138 and are pushed away from the sidewall. This provides two major advantages. First, this is a further mechanism to reduce coalescence, as the ridge 138 helps push the bubbles away from one another. Second, it gives the bubbles more time to establish themselves before they float up and are mixed by the impeller assembly. By giving the bubbles more time to form (i.e., increase resonance time prior to mixing) the bubble shape solidifies, which further aids in coalescence reduction once the bubbles are dispersed within the fluid of the flexible bag 30.

As illustrated, the ridge 138 radially extends away from the sidewall 133 a distance, and is located close to, but above the pores 137 of the sidewall. The distance the ridge extends from the sidewall 133, in embodiments, is such that the ridge 138 has a diameter less than the diameter of base 131. In further embodiments, the ridge extends such that it has a diameter equal to or greater than the diameter of base 131. The ridge may also have a curved or otherwise chamfered surface where it meets the sidewall 131. Having a curvature/chamfer, as opposed to a right angle, helps to guide the bubbles away from the sparger 130, such that disperse into the fluid of the flexible bag 30 more readily.

Figure 6B:
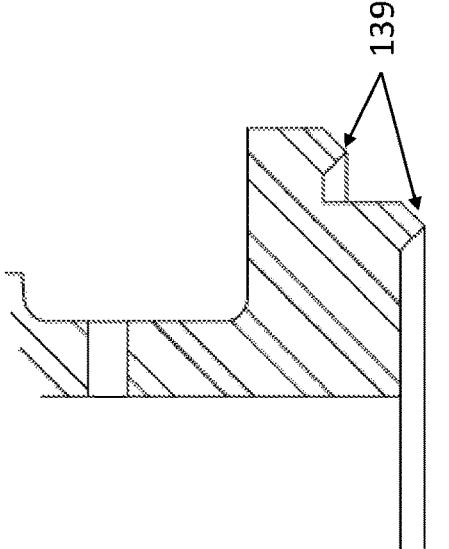
FIG. 6B is an enlarged view of section A of FIG. 6A, according to embodiments of the invention.
Figure 6A:
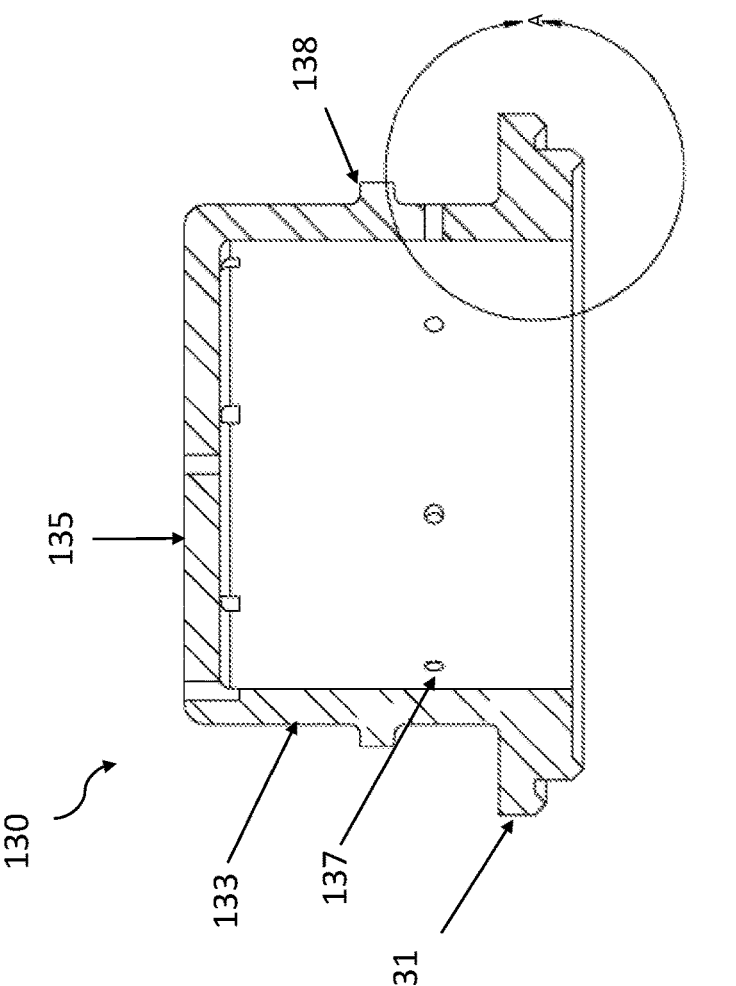
FIG. 6A illustrates a cross-sectional view of the sparger of FIGS. 5A-5B, according to embodiments of the invention.
Figure 7:
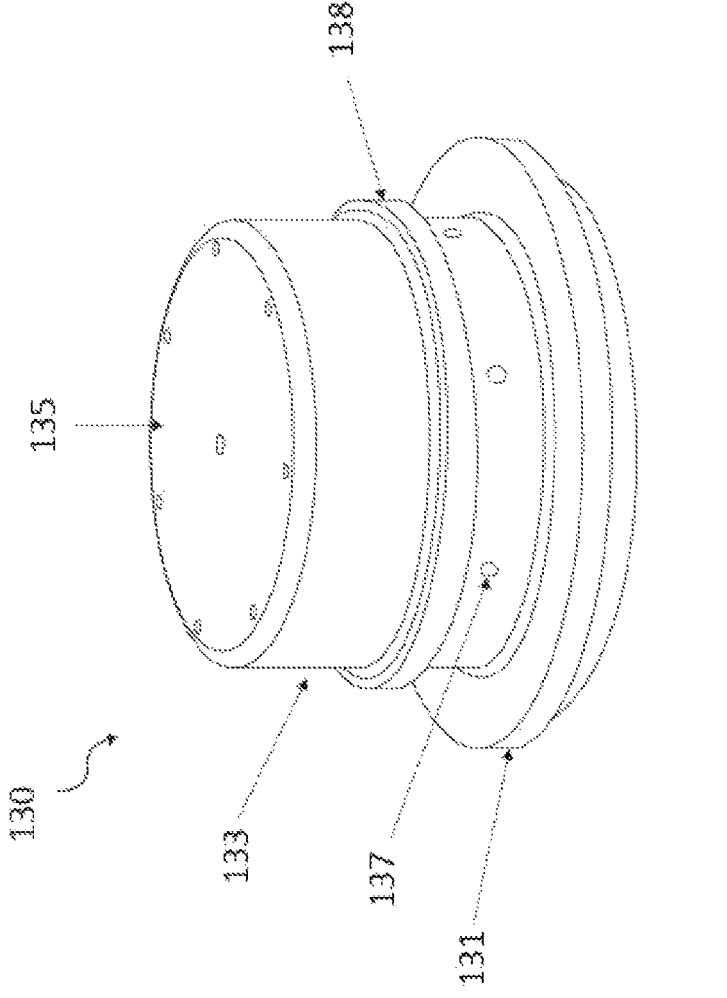
FIG. 7 is a perspective view of the sparger of FIGS. 5A-6B, according to embodiments of the invention.

With specific reference to FIG. 6B, base 131 includes bonding surfaces 139, which as illustrated are two circular regions having a generally triangular cross-section. When manufacturing the sparger assembly 100, each sparger 130 is placed on baseplate 126, and heat and/or vibrational forces are applied to sparger 130. The lower point of the triangle focuses this energy such that sparger 130 bonds to the baseplate 162 on both bonding surfaces 139.

FIGS. 8A-10 illustrate side, top, cross-sectional and perspective views of a sparger 130', according to further embodiments of the invention. Sparger 130' includes a base

131', with a sidewall 133' that projects up a height H2 from a top surface of the base 131'. The sidewall terminates at a top 135', which is a generally planar surface. As these figures illustrate, base 131' is generally circular in shape, and the sidewall 133' is cylindrically shaped, having a diameter that is less than the diameter of base 131' (although the diameters of the sidewall 133' and base 131' may be the same, or the diameter of the sidewall 133' can be larger than the base 131'). The sidewall 131' include pores 137' such that an introduced gas can bubble out of the sparger 130'. In particular embodiments, sidewall 133' includes a first array of pores 137' in a circular pattern at a height $H_p1$ and a second array of pores 137' in a circular pattern at a height $H_p2$, where $H_p2>H_p1$. In further embodiments, the two array of pores 137' do not have to be located at heights $H_p1$ and $H_p2$ but can have varying heights from the base 131'. Additionally, the top 135' includes an array of pores 137' in a circular pattern around its perimeter, with an additional central pore. The top 135' may optionally include an indentation or protuberance 136', which acts as a visual reference point to ensure that the sparger 130 is installed on the baseplate 162 in an appropriate geometry.

Figure 8B:
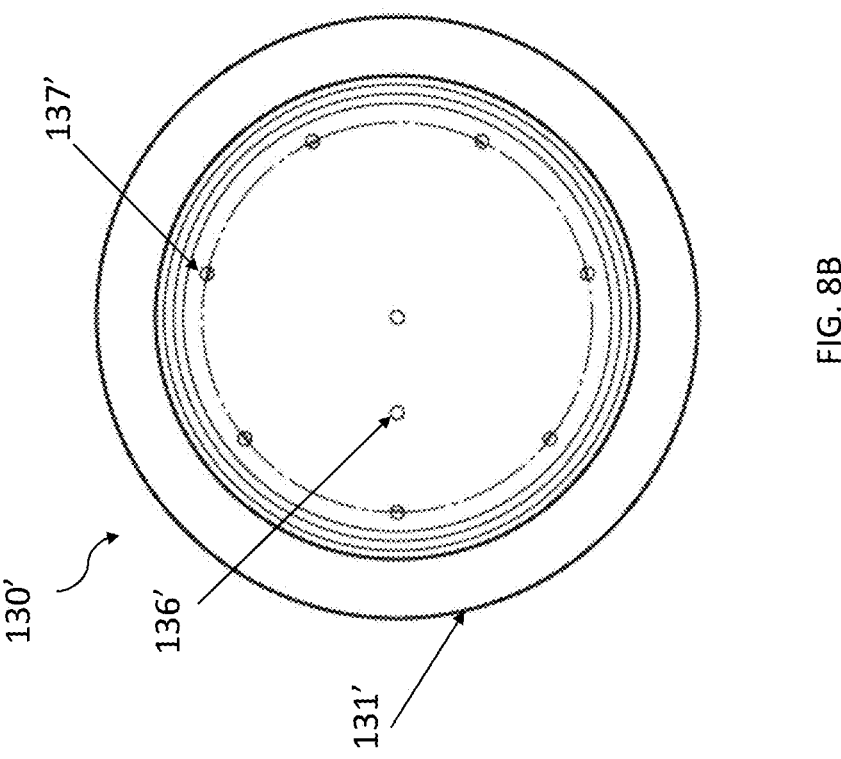
FIGS. 8A and 8B illustrate side and top views of a sparger, of the sparging assembly of FIGS. 2A-3, according to further embodiments of the invention.
Figure 8A:
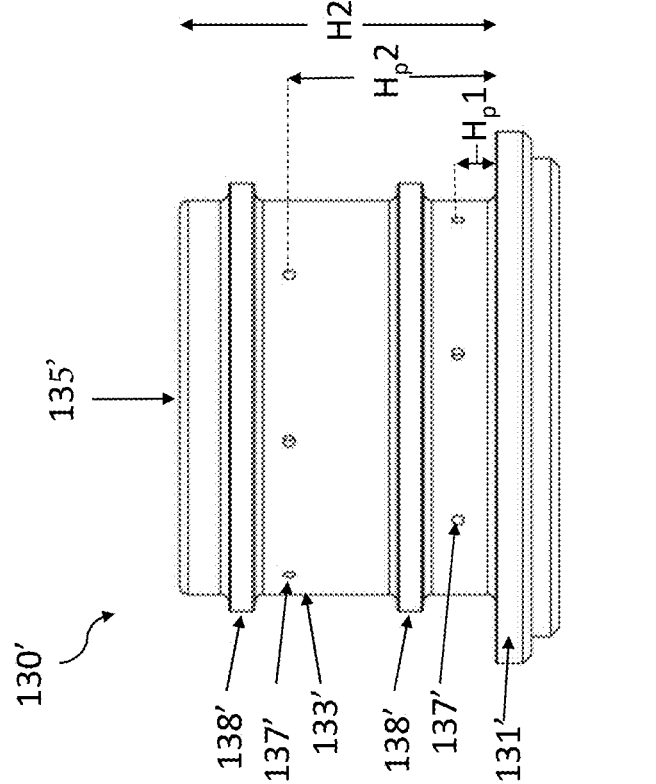

As best illustrated in FIG. 8A, the pores 137' located at height $H_p1$ are radially offset from the pores 137' located at height $H_p2$. By radially offsetting the pores there is a lower likelihood that bubbles coalesce. Said another way, as bubbles form and exit the sidewall 133' at height $H_p1$ they travel vertically upward. These bubbles are less likely to encounter bubbles formed by the pores 137' at height $H_p2$ because they are radially offset from one another (i.e., not located in parallel along a longitudinal axis of the sparger 130), thus reducing the likelihood of coalescence. Further, the pores 137' around the circumference of the top 135' are radially offset from the pores 137' located at height $H_p2$ for the same reasons. While it is noted that in one specific embodiment, there are seven circumferential pores and one central pore in the top 135', more or fewer pores are within the scope of the invention. Similarly, while the drawings illustrate seven pores in a circular pattern at a height $H_p1$ and $H_p2$, additional or fewer pores are within the scope of the invention.

Sparger 130' also includes a first ridge 138' that extends at least partially around the sidewall 133'. Ridge 138' is located above the array of pores 137' located in the sidewall 133' at height $H_p1$. A second ridge 138' is located above the array of pores 137' located in the sidewall 133' at height $H_p2$. These ridges 138' act a mechanism to guide the bubbles formed by the pores 137'. Specifically, as the bubbles form and exit the sidewall 133' they make contact with a bottom surface of the ridge 138' and are pushed away from the sidewall. This provides two major advantages. First, this is a further mechanism to reduce coalescence, as the ridge helps push the bubbles away from one another. Second, it gives the bubbles more time to establish themselves before they float up and are mixed by the impeller assembly. By giving the bubbles more time to form (i.e., increase resonance time prior to mixing) the bubble shape solidifies, which further aids in coalescence reduction once the bubbles are dispersed within the fluid of the flexible bag 30.

As illustrated, ridges 138' radially extends away from the sidewall 133' a distance, and are located close to, but above the pores 137' of the sidewall 133'. The distance the ridges extend from the sidewall 133', in embodiments, is such that ridges 138' have a diameter less than the diameter of base 131'. In further embodiments, the ridges have a diameter equal to or greater than that of the base 131'. The ridges 138' may also have a curved or otherwise chamfered surface where they meet the sidewall 131'. Having a curvature/chamfer, as opposed to a right angle, helps to guide the bubbles away from the sparger 130', such that disperse into the fluid of the flexible bag 30 more readily.

It is noted that while FIGS. 8A-10 illustrate two arrays of pores 137' and two respective ridges 138', the invention is not so limited. Additional arrays of pores 137' (e.g., three or more) and ridges 138' (e.g., three or more) are within the scope of the invention. The height H2 of sparger 130' can be varied to accommodate as many arrays of pores 137' and ridges 138 as desired, noting that the maximum height for H2 is constrained by the bottom surface of the impeller 122 (i.e., the top 135' of the sparger 130' cannot come into contact with the impeller 122.

Figure 9B:
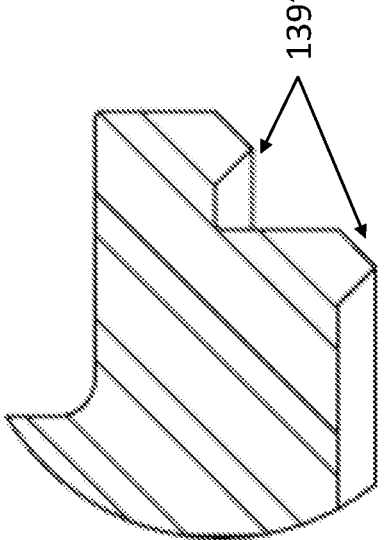
FIG. 9B is an enlarged view of section A of FIG. 9A, according to embodiments of the invention.
Figure 9A:
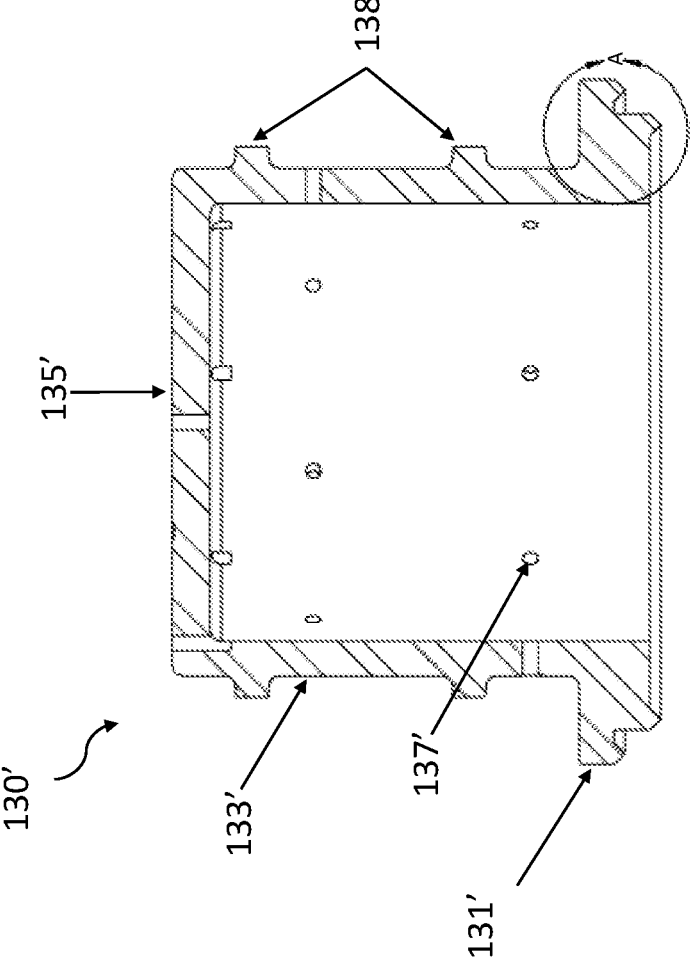
FIG. 9A illustrates a cross-sectional view of the sparger of FIGS. 8A-8B, according to embodiments of the invention.
Figure 10:
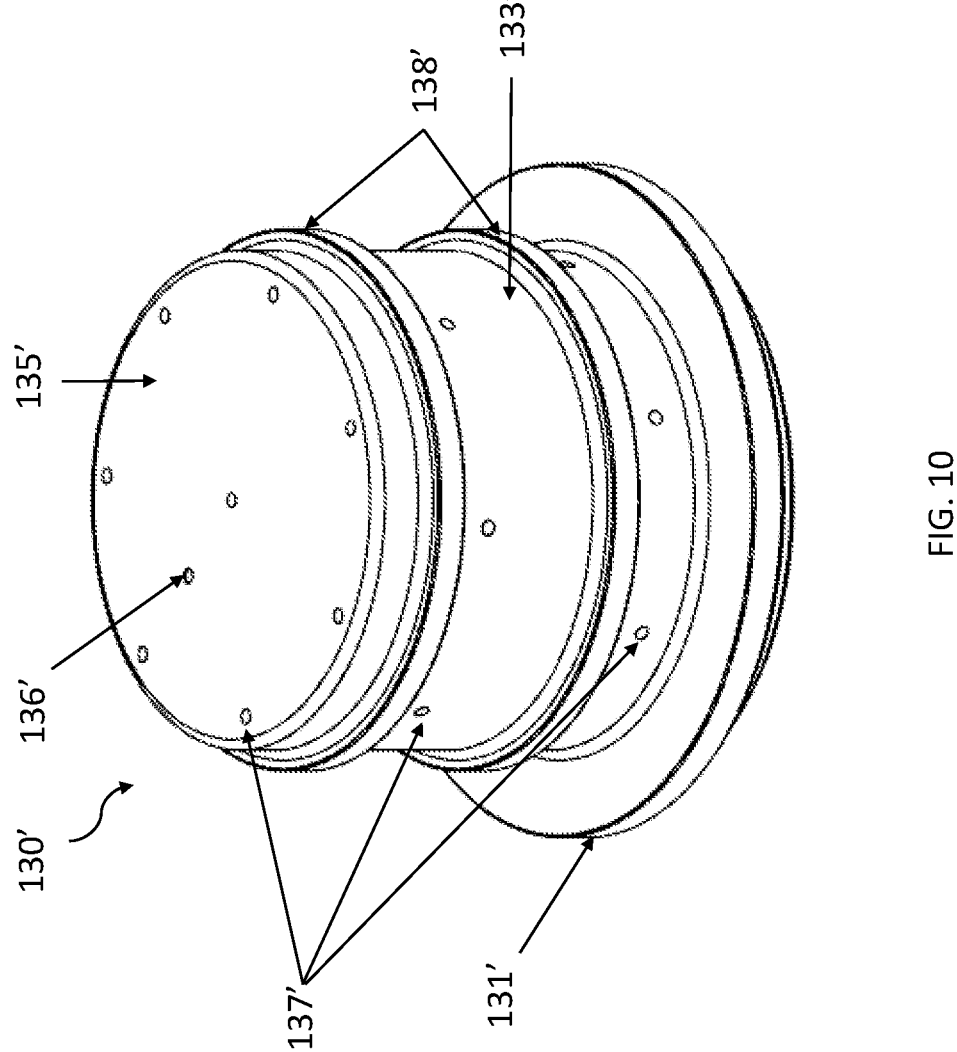
FIG. 10 is a perspective view of the sparger of FIGS. 8A-9B, according to embodiments of the invention.

With specific reference to FIG. 9B, base 131' includes bonding surfaces 139', which as illustrated are two circular regions having a generally triangular cross-section. When manufacturing the sparger assembly 100, each sparger 130' is placed on baseplate 126' and heat and/or vibrational forces are applied to sparger 130'. The lower point of the triangle focuses this energy such that sparger 130' bonds to the baseplate 162 on both bonding surfaces 139'.

With reference to the previously described embodiments, height H2 is larger than H1, such that sparger 130' is taller than sparger 130.

While the aforementioned embodiments illustrate and describe a sparger having a generally cylindrical sidewall, other shapes are within the scope of the invention. For example, the sidewall can curve outward such that the diameter of the sparger increasing. The sparger could have a mushroom-like shape, with a narrow lower stem that expands into a dome-like shape. Further, the sidewall does not need to have a circular cross-section shape, but can take other shapes, such as elliptical, square, rectangular, triangular, etc.

As the above disclosure provides, embodiments of the sparger assemblies disclosed herein provide increased kLa of a bioreactor system (i.e., achieving more efficient gas distribution) to support intensified cell culture and/or microbial applications. As compared to prior art designs, the three-dimensional spargers of the present invention provide a means to create a higher density of small bubbles that are less likely to coalesce. By ensuring a small bubble size with a high density, a higher surface area between the bubbles and the cell culture media is obtained, providing higher oxygen transfer and CO2 stripping within the culture media.

It is explicitly noted that the sparger assemblies disclosed herein may be utilized in connection with a number of existing impeller assemblies.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A sparger assembly for a bioprocessing system, comprising:
   a base; and
   a plurality of spargers connected to the base, each of the plurality of spargers having a generally cylindrical shape with a sidewall and a top that define the cylindrical shape, a plurality of pores disposed about the sidewall, and at least one ridge extending at least partially around a circumference of the sidewall that separates a portion of pores located on the sidewall below the at least one ridge from a portion of pores located on the sidewall above the at least one ridge.

2. The sparger assembly of claim 1, wherein:
   the plurality of pores are further disposed about the top.

3. The sparger assembly of claim 1, wherein:
   the pores of the sidewall include a first array of pores located at a first height from a top surface of the base.

4. The sparger assembly of claim 3, wherein:
   the pores of the sidewall include a second array of pores located at a second height from the top surface of the base, the second height being different than the first height.

5. The sparger assembly of claim 4, wherein:
   the second array of pores are radially offset in relation to the first array of pores.

6. The sparger assembly of claim 4, wherein:
   the at least one ridge includes a first ridge extending at least partially around the circumference of the sidewall, the first ridge located above the first array of pores.

7. The sparger assembly of claim 6, wherein:
   the at least one ridge includes a second ridge extending at least partially around the circumference of the sidewall, the second ridge located above the second array of pores.

8. The sparger assembly of claim 1, wherein:
   each of the plurality of spargers includes two bonding surfaces, the two bonding surfaces configured to bond with the base upon application of heat and/or vibratory forces.

9. An impeller and sparger assembly for a bioprocessing system, comprising:
   a sparger assembly comprising:
   a base;
   a plurality of spargers connected to the base, each sparger including a generally cylindrical shape with a sidewall, a top and a bottom that define the cylindrical shape, with the bottom having a surface directly on the base, and at least one ridge extending at least partially around a circumference of the sidewall that separates a portion of pores located on the sidewall below the at least one ridge from a portion of pores located on the sidewall above the at least one ridge; and
   an impeller assembly attached to the base.

10. The impeller and sparger assembly of claim 9, wherein:
   the impeller assembly includes a magnetic hub connected to the base; and
   an impeller connected to the magnetic hub.

11. A bioprocessing apparatus, comprising:

a flexible bag;

a sparging assembly comprising:

a base;

a plurality of spargers connected to the base, each sparger including a generally cylindrical shape with a sidewall, a top and a bottom that define the cylindrical shape, with the bottom having a surface disposed directly on the base, and at least one ridge extending at least partially around a circumference of the sidewall that separates a portion of pores located on the sidewall below the at least one ridge from a portion of pores located on the sidewall above the at least one ridge;

wherein the base is bonded to the flexible bag such that the plurality of spargers are located within the flexible bag; and an impeller assembly attached to the base, such that the impeller assembly is located within the flexible bag.

12. The bioprocessing apparatus of claim 11, wherein:

the base includes at least one input port, the at least one input port in fluid communication with the plurality of spargers.

13. The bioprocessing apparatus of claim 12, wherein:

the at least one input port is connectable to a gas source.

14. The bioprocessing apparatus of claim 13, wherein:

gas from the gas source is configured to exit through the plurality of pores and into the flexible bag.

* * * * *